United States Patent
Kasama

(10) Patent No.: US 9,299,235 B2
(45) Date of Patent: Mar. 29, 2016

(54) PORTABLE ELECTRONIC APPARATUS, AND FALLING PREDICTION METHOD

(71) Applicant: FUJITSU LIMITED, Kawasaki-shi, Kanagawa (JP)

(72) Inventor: Kouichirou Kasama, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 73 days.

(21) Appl. No.: 13/848,235

(22) Filed: Mar. 21, 2013

(65) Prior Publication Data

US 2013/0285813 A1  Oct. 31, 2013

(30) Foreign Application Priority Data

Apr. 27, 2012 (JP) .................................. 2012-104043

(51) Int. Cl.
| | | |
|---|---|---|
| *G08B 23/00* | (2006.01) | |
| *G08B 21/02* | (2006.01) | |
| *A61B 5/11* | (2006.01) | |
| *G06F 19/00* | (2011.01) | |
| *G08B 21/04* | (2006.01) | |
| *A61B 5/00* | (2006.01) | |

(52) U.S. Cl.
CPC .............. *G08B 21/02* (2013.01); *A61B 5/1117* (2013.01); *A61B 5/7275* (2013.01); *G06F 19/3406* (2013.01); *G06F 19/3418* (2013.01); *G08B 21/043* (2013.01); *G08B 21/0446* (2013.01); *A61B 5/1112* (2013.01); *A61B 5/6898* (2013.01); *A61B 2562/0219* (2013.01); *A61B 2562/0223* (2013.01)

(58) Field of Classification Search
CPC .................. A61B 2562/0219; A61B 5/6831; A61B 5/1117
USPC ........................................ 340/573.1; 600/595
See application file for complete search history.

(56) References Cited

U.S. PATENT DOCUMENTS

| | | | | |
|---|---|---|---|---|
| 5,669,392 | A  * | 9/1997 | Ljungstrom | .................. 600/510 |
| 2002/0116080 | A1 | 8/2002 | Brinbach et al. | |
| 2006/0195050 | A1 * | 8/2006 | Alwan et al. | .................. 600/595 |
| 2007/0068252 | A1 | 3/2007 | Honkura et al. | |

(Continued)

FOREIGN PATENT DOCUMENTS

| | | |
|---|---|---|
| JP | 2003-216743 A | 7/2003 |
| JP | 2006-198073 | 8/2006 |
| JP | 2007-093448 A | 4/2007 |
| JP | 2009-285816 A | 12/2009 |
| WO | 2011/004322 | 1/2011 |

OTHER PUBLICATIONS

Extended European Search Report of European Patent Application No. 13160762.4 dated Aug. 21, 2013.

(Continued)

*Primary Examiner* — Ojiako Nwugo
(74) *Attorney, Agent, or Firm* — Maschoff Brennan

(57) ABSTRACT

There is provided a computer-readable medium storing a program causing a processor to execute a procedure. The processor is provided in a portable electronic apparatus. The procedure includes detecting acceleration in the gravitational acceleration direction of the portable electronic apparatus, determining whether or not the acceleration in the gravitational acceleration direction is a threshold value or less, the threshold value being stored in a determination threshold value table, and raising an alarm for prediction of stumbling of a user when the acceleration in the gravitational acceleration direction is the threshold value or less.

4 Claims, 6 Drawing Sheets

(56) References Cited

U.S. PATENT DOCUMENTS

| | | | |
|---|---|---|---|
| 2008/0129518 A1 | 6/2008 | Carlton-Foss | |
| 2011/0248826 A1* | 10/2011 | Criel et al. | 340/10.1 |
| 2012/0101411 A1* | 4/2012 | Hausdorff et al. | 600/595 |

OTHER PUBLICATIONS

Miyoshi et al.,"Evaluation of Lower Limb Motor Function Using Wireless Motion Sensors—A Comparison of Normal Elderly Subjects and those Requiring Support Level 1", The IEEJ Journals C vol. 132, No. 1, Japan, the Institute of Electrical Engineers of Japan, vol. 132, pp. 104-110, Jan. 1, 2012. Translation of the summary indicated in the front page of this document. Cited in JP-OA mailed on Oct. 20, 2015 for corresponding Japanese Application No. 2012-104043.

Higashi et al.,"A Consideration of Features for Fatigue Estimation by Gait Analysis Using Accelerometer", The ISPJ Technical Reports, the 2010 edition 6, Japan, Information Processing Society of Japan, pp. 1-8, Mar. 8, 2011. Translation of the summary indicated in the front page of this document. Cited in JP-OA mailed on Oct. 20, 2015 for corresponding Japanese Application No. 2012-104043.

Office Action of Japanese Patent Application No. 2012-104043 dated Oct. 20, 2015. Translation of the relevant part of the Office Action.

* cited by examiner

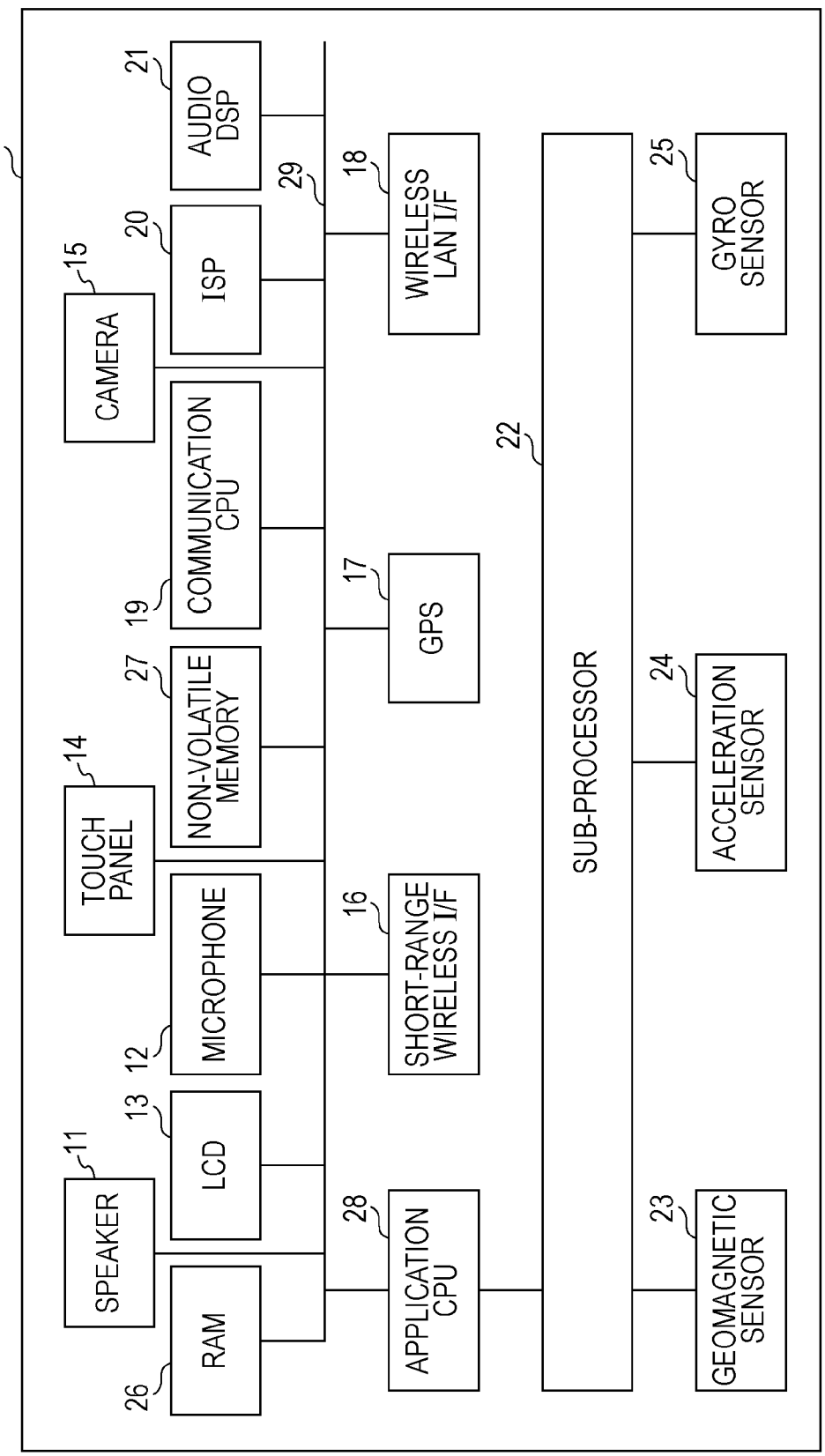

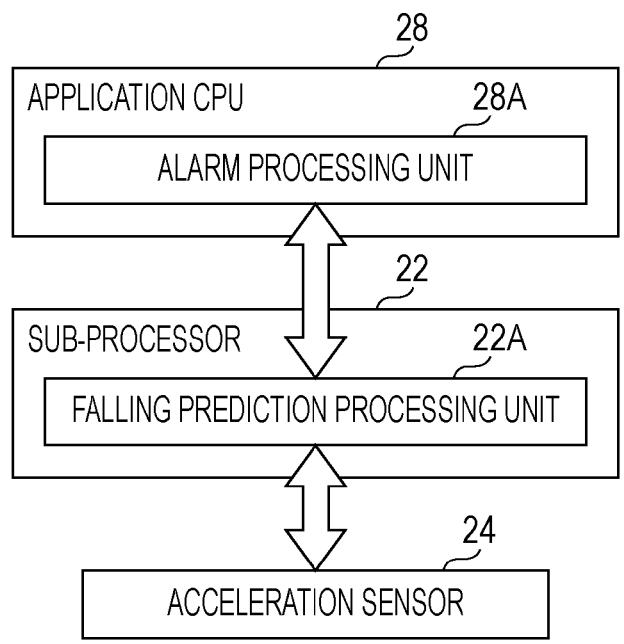

| WALKING FREQUENCY [Hz] | 1.3 | 1.5 | 2.0 | 2.2 | 2.5 | 3.0 |
|---|---|---|---|---|---|---|
| DETERMINATION THRESHOLD VALUE [mG] | 60 | 100 | 150 | 170 | 200 | 250 |

PORTABLE ELECTRONIC APPARATUS, AND FALLING PREDICTION METHOD

CROSS-REFERENCE TO RELATED APPLICATION

This application is based upon and claims the benefit of priority from the prior Japanese Patent Application No. 2012-104043 filed on Apr. 27, 2012, the entire contents of which are incorporated herein by reference.

FIELD

The embodiment is related to a portable electronic apparatus, and a falling prediction method.

BACKGROUND

In recent years, accidental falls in old age have been increasing year by year. Therefore, a supporting system that gives remotely guidance to a person to reduce accidental falls is widely known. In the supporting system, pressure sensors are arrayed on a floor, and the foot pressures of the user walking on the floor are measured by the pressure sensors. By using the measurement results on the foot pressures of the user, a degree of risk of falling may be determined.

Japanese Laid-open Patent Publication No. 2003-216743 is an example of the related arts.

SUMMARY

According to an aspect of the invention, a computer-readable medium storing a program causing a processor to execute a procedure, the processor being provided in a portable electronic apparatus, the procedure includes, detecting acceleration in the gravitational acceleration direction of the portable electronic apparatus, determining whether or not the acceleration in the gravitational acceleration direction is a threshold value or less, the threshold value being stored in a determination threshold value table, and raising an alarm for prediction of stumbling of a user when the acceleration in the gravitational acceleration direction is the threshold value or less.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 1 is a diagram illustrating an example of a portable terminal according to an embodiment;

FIG. 2 is diagram illustrating an example of a function configuration of an application CPU and a sub-processor;

FIG. 3 is a diagram illustrating an example of an acceleration table;

DESCRIPTION OF EMBODIMENT

Figures 4, 5:
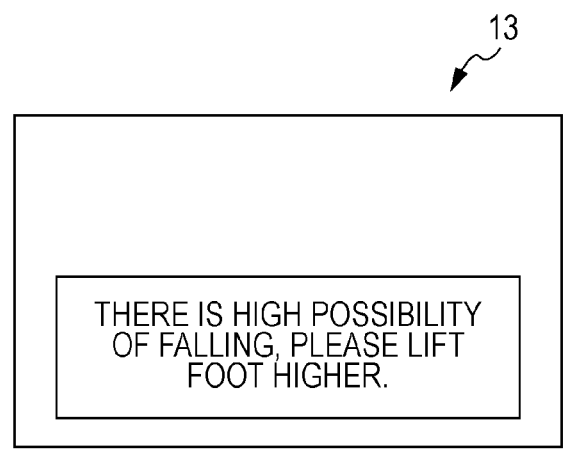
FIG. 4 is a diagram illustrating an example of a determination threshold value table.
FIG. 5 is a diagram illustrating an example of an alarm message.

However, in the supporting system described in the background, in order to determine the degree of risk of falling for the user, it is desirable that large scale equipment is arranged to lay the pressure sensors under the floor.

Therefore, it is desired to provide a falling prediction program, a portable electronic apparatus, and a falling prediction method which may allow a user to recognize an accidental fall beforehand.

A portable electronic apparatus, a falling prediction program, and a falling prediction method according to the embodiment are described below in detail with reference to accompanying drawings. The disclosed technique is not limited by the embodiment.

Embodiment

FIG. 1 is a diagram illustrating an example of a portable terminal 1 according to an embodiment. The portable terminal 1 that is illustrated in FIG. 1 is, for example, a mobile phone terminal such as a smartphone. The portable terminal 1 includes a speaker 11, a microphone 12, a liquid crystal display (LCD) 13, a touch panel 14, a camera 15, a short-range wireless interface (hereinafter referred to as I/F simply) 16, and a global positioning system (GPS) 17. In addition, the portable terminal 1 includes a wireless LAN I/F 18, a communication central processing unit (CPU) 19, an imaging signal processor (ISP) 20, an audio digital signal processor (DSP) 21, and a sub-processor 22. In addition, the portable terminal 1 includes, a geomagnetic sensor 23, an acceleration sensor 24, a gyro sensor 25, a random access memory (RAM) 26, a non-volatile memory 27, and an application CPU 28.

The LCD 13 displays various pieces of information on a screen. The touch panel 14 detects a touch operation on the screen of the LCD 13. The short-range wireless I/F 16 is an interface that is responsible for a short-range wireless communication function. The GPS 17 is a system that measures a current position of the portable terminal 1 using a GPS satellite. The wireless LAN I/F 18 is an interface that is responsible for a wireless LAN function. The communication CPU 19 is a CPU that is responsible for various communication functions such as a mobile phone communication function. The ISP 20 is a processor that is responsible for image signal processing. The audio DSP 21 is a processor that is responsible for audio signal processing. The sub-processor 22 is, for example, an external processor that executes a falling prediction program. The geomagnetic sensor 23 is, for example, a sensor that detects orientation of the portable terminal 1.

The acceleration sensor 24 is a sensor that detects, for example, acceleration in each direction of three axes, "x" axis, "y" axis, and "z" axis of the portable terminal 1. The gyro sensor 25 is, for example, a sensor that detects angular velocities of the three axes. The non-volatile memory 27 stores various programs such as the falling prediction program. The RAM 26 stores various pieces of information. The application CPU 28 controls the whole portable terminal 1. A bus 29 connects various devices in the portable terminal 1 such as the application CPU 28 and the RAM 26, each other.

FIG. 2 is a diagram illustrating an example of a function configuration of the sub-processor 22 and the application CPU 28. The sub-processor 22 and the application CPU 28 read the falling prediction program that is stored in the non-volatile memory 27 and configure various processes as functions in accordance with the read falling prediction program. The sub-processor 22 that is illustrated in FIG. 2 operates a falling prediction processing unit 22A as a function. In addition, the application CPU 28 operates an alarm processing unit 28A as a function.

The RAM 26 stores an acceleration table 40 that is illustrated in FIG. 3. FIG. 3 is diagram illustrating an example of the acceleration table. The acceleration table 40 that is illustrated in FIG. 3 sequentially stores data 40A, 40B, and 40C of acceleration in the directions of "x" axis, "y" axis, and "z" axis, respectively, and data 40D of acceleration in a gravitational acceleration direction 40D for each sampling cycle. The falling prediction processing unit 22A detects the acceleration in the directions of "x" axis, "y" axis, and "z" axis by the acceleration sensor 24 for each sampling cycle, for example, 20 msec cycle, and stores the data of acceleration in the directions of the three axes and the data of acceleration in the gravitational acceleration direction, in the acceleration table 40 for each 20 m/sec cycle. The acceleration table 40 employs, for example, a buffer system that sequentially stores sampling data for each set of lines from the first line to the 50th line. The acceleration table 40 may store 50 acceleration data that are obtained in a cycle of 20 msec. That is, acceleration data for 10 second may be stored.

The falling prediction processing unit 22A sequentially stores the acceleration data in the list from the first line to the 50th line, which are detected for 20 m/sec cycles. In addition, the falling prediction processing unit 22A deletes the acceleration data that has been stored in the first line, moves forward each acceleration data in the list so as to leave the space of the 50th line for a coming new data, and stores the new acceleration data in the 50th line when the next acceleration is detected after the acceleration data has been stored in the 50th line of the acceleration table 40. As described above, the falling prediction processing unit 22A repeatedly executes the operation to delete an acceleration data of the first line, leave the space of the 50th line, and sequentially store a new acceleration data in the 50th line.

In addition, the falling prediction processing unit 22A calculates acceleration in the gravitational acceleration direction on the basis of the acceleration in the directions of "x" axis, "y" axis, and "z" axis for each of the sampling cycles. In addition, the falling prediction processing unit 22A sequentially stores the data of acceleration in the gravitational acceleration direction in the acceleration table 40 for the sampling cycles. In addition, the falling prediction processing unit 22A measures the number of steps in the previous one minute, and calculates a walking frequency (Hz) by dividing the number of steps in the previous one minute by 60. The walking frequency is an index that corresponds to a walking pitch of the user.

In addition, the non-volatile memory 27 stores a determination threshold value table 50 that is illustrated in FIG. 4. FIG. 4 is a diagram illustrating an example of the determination threshold value table. The determination threshold value table 50 that is illustrated in FIG. 4 stores a determination threshold value 50B depending on a walking frequency 50A. The determination threshold value is a threshold value that is used to determine acceleration in a gravitational acceleration direction, which predicts falling of the user at the time of walking beforehand. The falling of the user is often caused by a stumble at the time of walking, and the stumble is caused when a foot of the user is not sufficiently lifted high. Therefore, whether or not the foot of the user is sufficiently lifted high is determined by landing impact of the user, that is, determined by magnitude of the acceleration in the gravitational acceleration direction in the portable terminal 1 carried by the user. Therefore, a threshold value is set beforehand, which is used to determine whether or not acceleration in the gravitational acceleration direction of the user is the acceleration that is likely to causes the user to be fallen at the time of walking. For example, when acceleration in the gravitational acceleration direction at the time of normal walking is set as a walking reference value, the determination threshold value that is used to determine that a degree of risk of falling is high is smaller than the walking reference value.

In addition, the determination threshold value increases in proportion to a walking pitch of the user, that is, a walking frequency. Therefore, the falling prediction processing unit 22A calculates a walking frequency of the user, and determines the determination threshold value 50B that corresponds to the calculated walking frequency 50A from the determination threshold value table 50. In addition, the falling prediction processing unit 22A determines that current walking of the user is walking having a high level of risk of falling when a state in which the acceleration in the gravitational acceleration direction is the determination threshold value or less continues for five minutes or more.

In addition, the alarm processing unit 28A in the application CPU 28 indicates a high level of risk of falling using the speaker 11 and the LCD 13 when it is determined that the current walking of the user is walking having a high level of risk of falling. FIG. 5 is a diagram illustrating an example of an alarm message. As illustrated in FIG. 5, the alarm processing unit 28A displays message, etc. that indicates "There is high possibility of falling, please lift foot higher", etc. on the screen of the LCD 13. In addition, the alarm processing unit 28A acoustically outputs the warning tone, etc., indicating a high level of risk of falling through the speaker 11.

Figure 6:
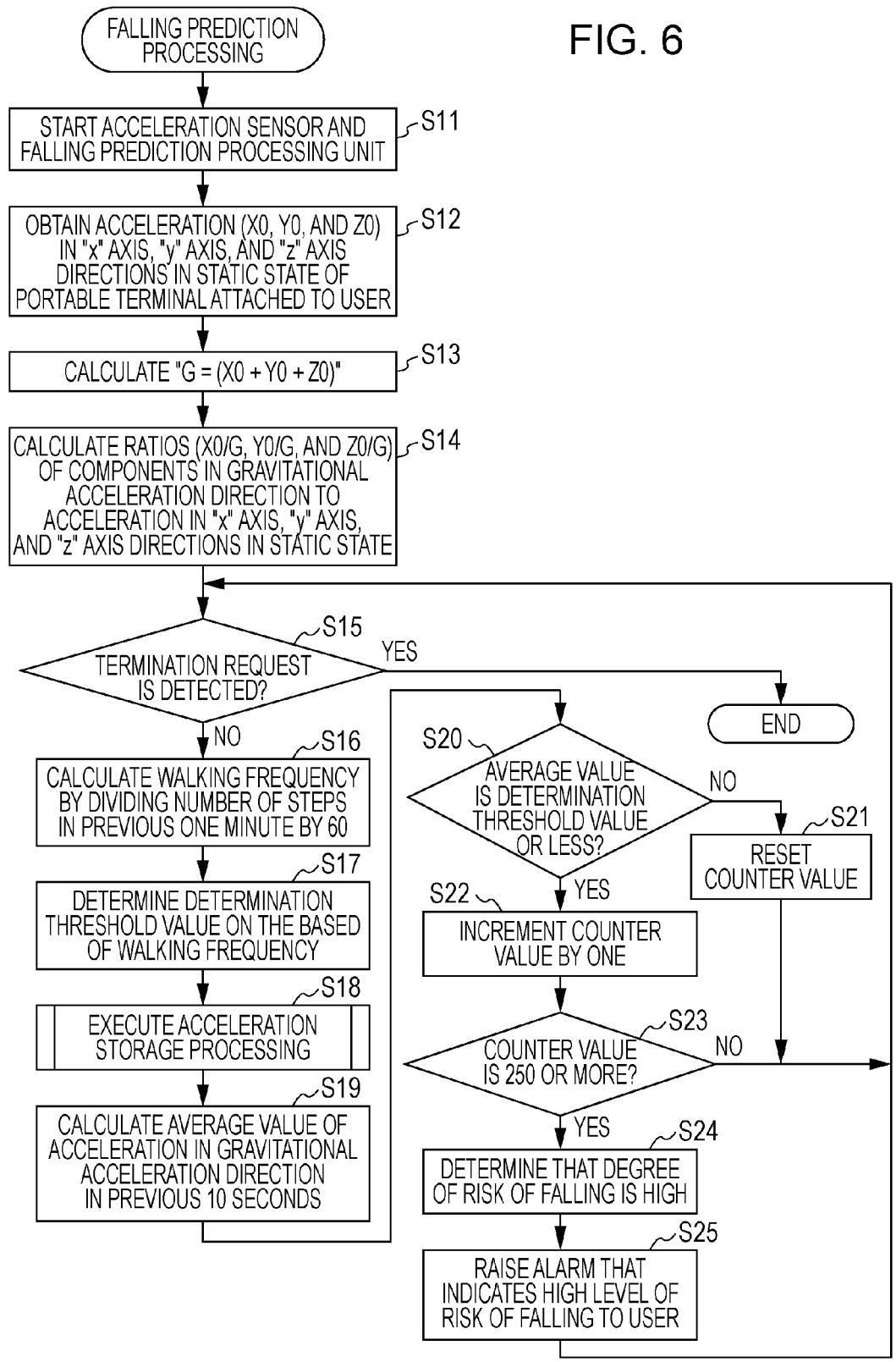
FIG. 6 is a flowchart illustrating an example of an operation on the sub-processor side of a portable terminal, which is related to falling prediction processing.

An operation of the portable terminal 1 according to the embodiment is described below. FIG. 6 is a flowchart illustrating an example of an operation on the sub-processor 22 side of the portable terminal 1, which is related to falling prediction processing. The falling prediction processing illustrated in FIG. 6 raises an alarm, which allows a user to predict stumbling, depending on acceleration in the gravitational acceleration direction of the portable terminal 1 carried by the user.

In FIG. 6, the sub-processor 22 starts the acceleration sensor 24 and the falling prediction processing unit 22A (Step S11). The falling prediction processing unit 22A detects accelerations X0, Y0, and Z0 in directions of "x" axis, "y" axis, and "z" axis, respectively, using the acceleration sensor 24 in a static state of the portable terminal 1 that is attached to the user's clothes (Step S12). The falling prediction processing unit 22A calculates "G=(X0+Y0+Z0)" by combining the accelerations X0, Y0, and Z0 in the directions of "x" axis, "y" axis Y0, and the direction of "z" axis, respectively, in the static state (Step S13).

The falling prediction processing unit 22A calculates ratios (X0/G, Y0/G, and Z0/G) of components in the gravitational acceleration direction, to the acceleration in the directions of "x" axis, "y" axis, and "z" axis in the static state (Step S14). The falling prediction processing unit 22A stores the ratio (X0/G, Y0/G, Z0/G) of the components in the gravitational acceleration direction, in the RAM 26. The falling prediction processing unit 22A determines whether or not a termination request of the falling prediction processing is detected (Step S15).

The falling prediction processing unit 22A calculates a walking frequency of the user who is currently walking (Step S16) when a termination request of the falling prediction processing is not detected (No in Step S15). The falling prediction processing unit 22A measures the number of steps in the previous minute of the user who is currently walking, and calculates a walking frequency (Hz) by dividing the number of steps by 60. In addition, the falling prediction processing unit 22A determines the determination threshold value 50B that corresponds to the walking frequency 50A from the determination threshold value table 50 (Step S17). As a result, the falling prediction processing unit 22A may set a determination threshold value that corresponds to the walking pitch of the user who is currently walking.

Figure 7:
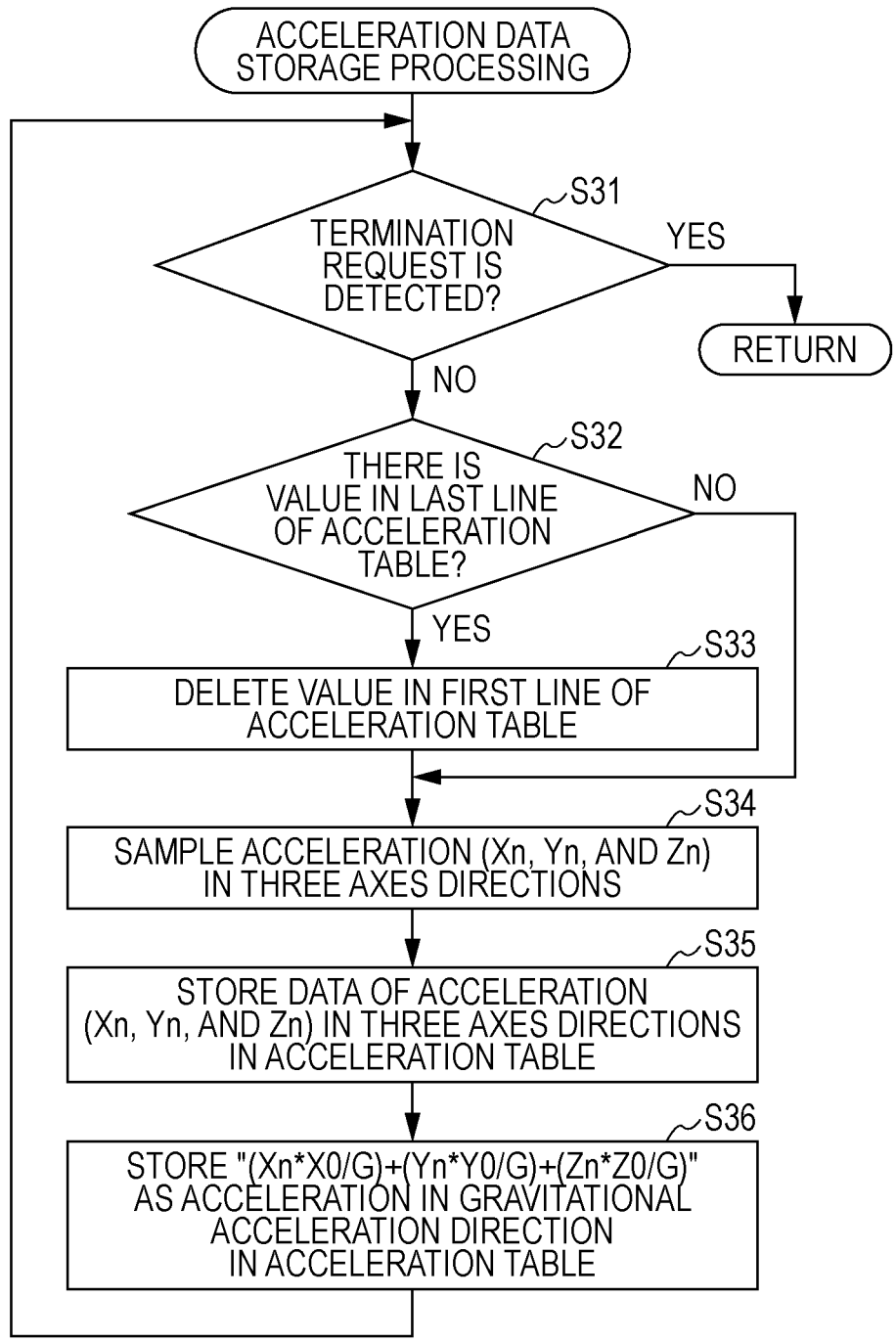
FIG. 7 is a flowchart illustrating an example of an operation on the sub-processor side of a portable terminal, which is related to an operation for storing acceleration data.

The falling prediction processing unit 22A executes the acceleration storage processing that is illustrated in FIG. 7 (Step S18). The falling prediction processing unit 22A calculates an average value of acceleration in the gravitational acceleration direction in the previous 10 seconds in the acceleration table 40 (Step S19) after the acceleration storage processing is executed. The falling prediction processing unit 22A determines whether or not the calculated average value of the acceleration in the gravitational acceleration direction is the determination threshold value or less (Step S20). The falling prediction processing unit 22A resets a counter value (Step S21) when the average value of the acceleration in the gravitational acceleration direction is not the determination threshold value or less (No in Step S20), and causes the flow to proceed to Step S15 to determine whether or not a termination request is detected. The counter value is incremented by one for each 20 seconds for which an acceleration data in the gravitational acceleration direction is sequentially stored on the basis of the acceleration data of the three axes that are pieces of sample data. In addition, the counter value that is used to determine that a degree of risk of falling is high is, for example, 250 (for example, five minutes).

The falling prediction processing unit 22A determines walking of the user is walking having a high level of risk of falling and increments the counter value by one (Step S22) when the average value of the acceleration in the gravitational acceleration direction is the determination threshold value or less (Yes in Step S20). In addition, the falling prediction processing unit 22A determines whether or not the counter value is 250 or more (Step S23). The falling prediction processing unit 22A determines the state in which a degree of risk of falling is high continues for five minutes or more and determines that the walking of the user is walking having a high level of risk of falling (Step S24) when the counter value is 250 or more (Yes in Step S23).

The falling prediction processing unit 22A determines that the walking of the user is walking having a high level of risk of falling, raises an alarm that indicates that a degree of risk of falling is high (Step S25), and causes the flow to proceed to Step S15 to determine whether or not a termination request is detected. To raise an alarm, the LCD 13, the speaker 11, etc. may be used. The falling prediction processing unit 22A terminates the processing operation that is illustrated in FIG. 6 when a termination request is detected (Yes in Step S15). In addition, the falling prediction processing unit 22A causes the flow to proceed Step S15 to determine whether or not a termination request is detected when the counter value is not 250 or more (No in Step S23).

The falling prediction processing unit 22A of the falling prediction processing that is illustrated in FIG. 6 calculates acceleration in the gravitational acceleration direction of the user, on the basis of the accelerations in the directions of three axes of the user, which are detected for each 20 m/sec cycle. In addition, the falling prediction processing unit 22A sequentially stores data of acceleration in the gravitational acceleration direction for each of the 20 m/sec cycles, in the acceleration table 40. In addition, the falling prediction processing unit 22A determines whether or not an average value of acceleration in the gravitational acceleration direction in the 10 seconds portion (data for 10 seconds), which are stored in the acceleration table 40 is the determination threshold value or less. The falling prediction processing unit 22A determines that the walking of the user is walking having a high level of risk of falling, and raises an alarm that indicates the degree of risk of falling is high when the state in which the average value of the acceleration in the gravitational acceleration direction is the determination threshold value or less continues for five seconds or more. As a result, the user may recognize that the current walking is walking having a high level of risk of falling, beforehand, on the basis of the alarm.

The falling prediction processing unit 22A measures the number of steps of the user in the previous minute, and calculates a walking frequency by dividing the number of steps by 60. In addition, the falling prediction processing unit 22A determines a determination threshold value depending on a walking frequency from the determination threshold value table 50. As a result, the user may set a determination threshold value depending on a current walking pitch because the determination threshold value is changed depending on a current walking frequency.

FIG. 7 is a flowchart illustrating an example of an operation on the sub-processor 22 side of the portable terminal 1, which is related to the operation for storing acceleration data. The acceleration storage processing that is illustrated in FIG. 7 is processing to sequentially store data of acceleration in the directions of "x" axis, "y" axis, and "z" axis, and data of acceleration in the gravitational acceleration direction in the acceleration table 40 for each 20 m/sec cycle.

The falling prediction processing unit 22A determines whether or not a termination request is detected (Step S31). The falling prediction processing unit 22A determines whether or not there is a value in the last line of the acceleration table 40 (Step S32) when a termination request is not detected (No in Step S31). The falling prediction processing unit 22A deletes the value in the first line of the acceleration table 40 (Step S33) when there is a value in the last line of the acceleration table 40 (Yes in Step S32). In addition, the falling prediction processing unit 22A detects acceleration Xn in the direction of "x" axis, acceleration Yn in the direction of "y" axis, and acceleration Zn in the direction of "z" axis in the present time "n" by the acceleration sensor 24 (Step S34).

The falling prediction processing unit 22A stores the data of acceleration Xn, Yn, and Zn in the directions of "x" axis, "y" axis and "z" axis, respectively, in the acceleration table 40 (Step S35). In addition, the falling prediction processing unit 22A calculates acceleration in the gravitational acceleration direction on the basis of the data of acceleration Xn, Yn, and Zn in the directions of "x" axis, "y" axis, and "z" axis, respectively, and the ratio (X0/G, Y0/G, and Z0/G) of the axes in the gravitational acceleration direction in the static state. In addition, the falling prediction processing unit 22A associates the calculated acceleration in the gravitational acceleration direction with the acceleration in the directions of Xn, Yn, and Zn of the three axes and stores the associated acceleration data in the acceleration table 40 (Step S36). The falling prediction processing unit 22A calculates acceleration in the gravitational acceleration direction on the basis of "(Xn*X0/G)+(Yn*Y0/G)+(Zn*Z0/G)". In addition, the falling prediction processing unit 22A stores the calculated acceleration data in the acceleration table 40, and then causes the flow to proceed to Step S31 to determine whether or not a termination request is detected.

In addition, the falling prediction processing unit 22A causes the flow to proceed to Step S34 to detects acceleration in the directions of the three axes when there is no value in the last line of the acceleration table 40.

The falling prediction processing unit 22A performing the acceleration storage processing illustrated in FIG. 7 calculates acceleration in the gravitational acceleration direction on the basis of the acceleration in the directions of the three axes, which are detected for each 20 m/sec cycle, and sequentially stores the calculated acceleration in the gravitational acceleration direction in the acceleration table 40. As a result, the acceleration in the gravitational acceleration direction for the previous 10 seconds, which are related to the user may be stored in the acceleration table 40.

The falling prediction processing unit 22A according to the embodiment determines whether or not an average value of the acceleration in the gravitational acceleration direction in the previous 10 seconds, which are stored in the acceleration table 40, is the determination threshold value or less. The falling prediction processing unit 22A determines that the walking of the user is walking having a high level of risk of falling and raises an alarm that indicates a degree of risk of falling is high when the state in which the average value of the acceleration in the gravitational acceleration direction is the determination threshold value or less continues for five minutes or more. As a result, the user may recognize beforehand that current walking is walking having a high level of risk of falling, on the basis of the alarm. Thus, the accidental falls of the user are reduced beforehand by calling attention to the user. In addition, the occurrence of falling may be predicted under a low resource environment such as the portable terminal 1 without a conventional large-scale system.

The falling prediction processing unit 22A measures the number of steps of the user in the previous minute, and calculates a walking frequency by dividing the number of steps by 60. In addition, the falling prediction processing unit 22A determines a determination threshold value depending on a walking frequency because acceleration increases as the walking frequency increases. As a result, the user may set the determination threshold value as a current walking pitch.

In the above-described embodiment, the portable terminal 1 such as a smartphone is illustrated, and alternative, for example, a mobile phone, a portable game terminal, a tablet terminal, a portable terminal that does not include a communication function, etc. may be employed for the above-described embodiment.

In addition, in the above-described embodiment, acceleration in the directions of the three axes of the user are detected for each 20 m/sec cycle, and alternatively, a detection cycle of the acceleration may be changed as appropriate instead of the 20 m/sec cycle.

In addition, in the above-described embodiment, acceleration data in the gravitational acceleration direction in the previous 10 seconds are stored in the acceleration table 40, and it is determined whether or not the average value of the acceleration in the gravitational acceleration direction in the previous 10 seconds is the determination threshold value or less, for each 20 m/sec cycle. The cycle of the determination operation between the average value and the determination threshold value is not limited to a 20 m/sec cycle, and a highly accurate determination operation may be realized by shortening the cycle of the determination operation. In addition, a power consumption amount that is desired for the determination operation may be reduced by elongating the cycle of the determination operation.

In addition, in the above-described embodiment, the counter value is reset when the average value of the acceleration in the gravitational acceleration direction exceeds the determination threshold value even once until the counter value becomes 250 in a row, and alternatively, for example, the counter value may be reset when the average value exceeds the determination threshold value in a row.

In addition, in the above-described embodiment, it is determined, using the counter value, whether or not the state in which the average value of the acceleration in the gravitational acceleration direction is the determination threshold value or less continues for a certain time period, and alternatively, a timer may be used to measure a time instead of use of the counter value.

In addition, in the above-described embodiment, it is determined that the walking of the user is walking having a high level of risk of falling when the state in which the average value of the acceleration in the gravitational acceleration direction is the determination threshold value or less continues for five minutes or more, and alternatively, the time may be changed as appropriate instead of five minutes.

In addition, in the above-described embodiment, the acceleration in the gravitational acceleration direction is calculated on the basis of the acceleration in the directions of the three axes, which are obtained by the acceleration sensor 24 that is built in the portable terminal 1. Alternatively, the portable terminal may collect acceleration in the direction of the three axes, which are related to the user, from an external acceleration sensor and calculate acceleration in the gravitational acceleration direction on the basis of the collected acceleration in the directions of the three axes even when an acceleration sensor is not built in the portable terminal 1.

In addition, each of the illustrated configuration elements of each of the units may not be configured physically as illustrated in the accompany drawings. That is, a specific example of distribution or integration of the units is not limited to the illustrated example, and all or a part of the units may be configured to be functionally or physically distributed or integrated in a given unit in accordance with various loads, usage, etc.

In addition, all or a part of various processing functions that are executed in each of the devices may be executed on a CPU (or a microcomputer such as a micro processing unit (MPU) and a micro controller unit (MCU)). In addition, the all or a part of the various processing functions may be executed on a program that analyzes and executes the various processing functions by a CPU (or microcomputer such as MPU and MCU), or on hardware by wired logic.

Figure 8:
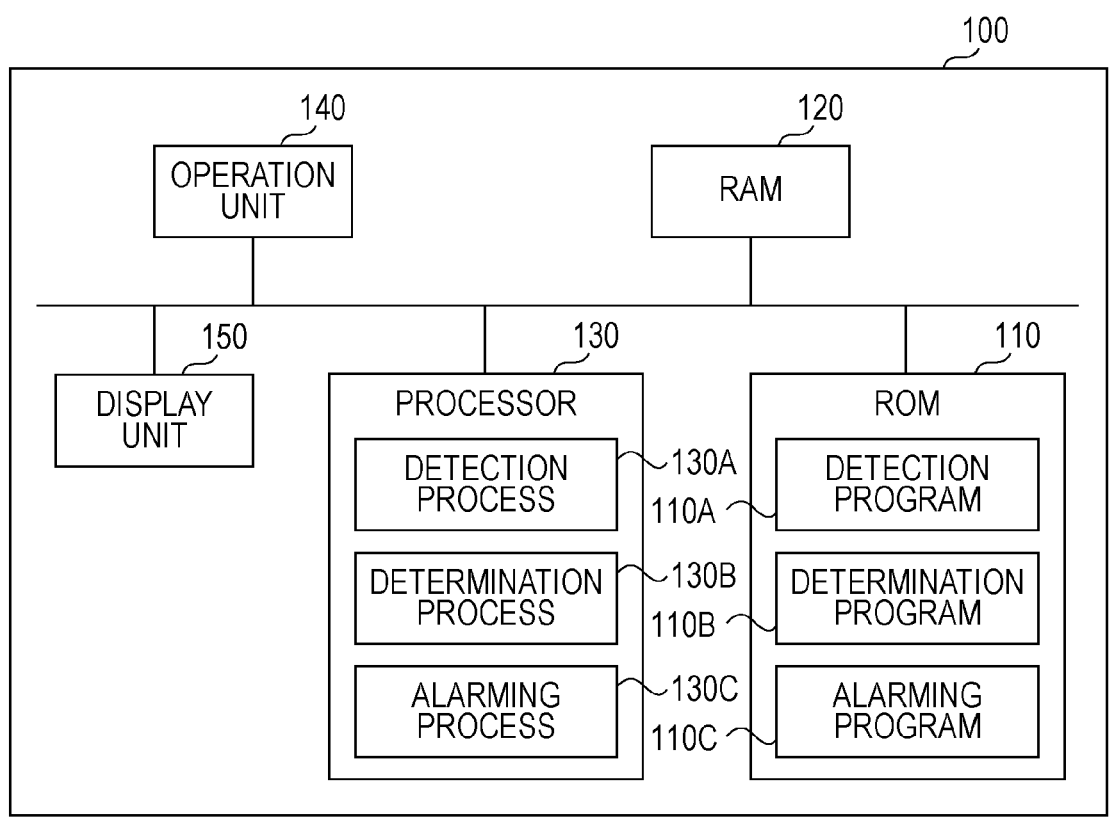
FIG. 8 is a diagram illustrating an electronic apparatus that executes a falling prediction program.

The various pieces of processing that are described in the embodiment may be realized when an electronic apparatus executes a program that is prepared beforehand. Therefore, an example of an electronic apparatus that executes a program having a function similar to that of the above-described embodiment is described below. FIG. 8 is a diagram illustrating an electronic apparatus that executes the falling prediction program.

An electronic apparatus 100 that executes the falling prediction program and is illustrated in FIG. 8 includes a read-only memory (ROM) 110, a RAM 120, a processor 130, an operation unit 140, and a display unit 150.

In addition, in the ROM 110, the falling prediction program that fulfills a function similar to that of the above-described embodiment is stored beforehand. The falling prediction program may be recorded to a recording medium that is readable by a drive (not illustrated) instead of the ROM 110. In addition, as the recording medium, for example, a portable recording medium such as a CD-ROM, a DVD disk, a USB memory, and an SD card, and a semiconductor memory such as a flash memory may be employed. As the falling prediction program, as illustrated in FIG. 8, there are a detection program 110A, a determination program 110B, and an alarming program 110C. The programs 110A, 110B, and 110C may be integrated or distributed as appropriate.

In addition, the processor 130 reads the programs 110A, 110B, and 110C from the ROM 110 and executes the each of the read programs. In addition, as illustrated in FIG. 8, the processor 130 causes the programs 110A, 110B, and 110C to function as a detection process 130A, a determination process 130B, and an alarming process 130C, respectively.

The processor 130 detects acceleration in the gravitational acceleration direction of the electronic apparatus. The processor 130 determines whether or not the data of acceleration in the gravitational acceleration direction is a threshold value or less that is stored in the RAM 120. The processor 130 raises an alarm that indicates the occurrence of falling of the user when the acceleration in the gravitational acceleration direction is the threshold value or less. As a result, the user may recognize the occurrence of falling beforehand on the basis of the alarm predicting the occurrence of falling.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A non-transitory computer-readable medium storing a program causing a processor to execute a procedure, the processor being provided in a portable electronic apparatus, the procedure comprising:
    detecting acceleration in a gravitational acceleration direction of the portable electronic apparatus;
    detecting a walking frequency of a user;
    determining whether or not the acceleration in the gravitational acceleration direction is a threshold value or less for a predetermined amount of time, the threshold value being stored in a determination threshold value table;
    raising an alarm for predicting stumbling of the user when the acceleration in the gravitational acceleration direction is the threshold value or less; and
    changing the threshold value so that the threshold value is increased as the detected walking frequency is increased, the threshold value being calculated depending on an average value of the detected walking frequency in a certain time period,
    wherein the detecting of the acceleration in the gravitational acceleration direction includes calculating a ratio of acceleration for each coordinate axis, the ratio of acceleration for each coordinate axis corresponding to detected acceleration in each coordinate axis as detected by an acceleration sensor of the portable electronic apparatus being held by the user in a static state with respect to the sum of the detected acceleration in all of the coordinate axes,
    wherein the acceleration in the gravitational acceleration direction of the portable electronic apparatus is calculated based on the calculated ratio of acceleration for each coordinate axis with respect to the gravitational acceleration direction.

2. A non-transitory computer-readable medium storing a program according to claim 1, wherein
    in the raising of an alarm, the alarm is for prediction of stumbling of the user when a state in which the acceleration in the gravitational acceleration direction is the threshold value or less continues for a certain time period.

3. A portable electronic apparatus comprising:
    a processor that executes processing including,
    detecting acceleration in a gravitational acceleration direction of the portable electronic apparatus;
    detecting a walking frequency of a user;
    determining whether or not the acceleration in the gravitational acceleration direction is a threshold value or less for a predetermined amount of time, the threshold value being stored in a determination threshold value table;
    causing an alarm for prediction of stumbling of the user when the acceleration in the gravitational acceleration direction is the threshold value or less; and
    changing the threshold value so that the threshold value is increased as the detected walking frequency is increased, the threshold value being calculated depending on an average value of the detected walking frequency in a certain time period,
    wherein the detecting of the acceleration in the gravitational acceleration direction includes calculating a ratio of acceleration for each coordinate axis, the ratio of acceleration for each coordinate axis corresponding to detected acceleration in each coordinate axis as detected by an acceleration sensor of the portable electronic apparatus being held by the user in a static state with respect to the sum of the detected acceleration in all of the coordinate axes,
    wherein the acceleration in the gravitational acceleration direction of the portable electronic apparatus is calculated based on the calculated ratio of acceleration for each coordinate axis with respect to the gravitational acceleration direction.

4. A falling prediction method causing a portable electronic apparatus to execute processing, the processing comprising:
    detecting acceleration in the gravitational acceleration direction of the portable electronic apparatus being carried by a user;
    detecting a walking frequency of the user;
    determining whether or not the acceleration in the gravitational acceleration direction is a threshold value or less for a predetermined amount of time, the threshold value being stored in a determination threshold value table;
    raising an alarm for prediction of stumbling of the user when the acceleration in the gravitational acceleration direction is the threshold value or less; and
    changing the threshold value so that the threshold value is increased as the detected walking frequency is increased, the threshold value being calculated depending on an average value of the detected walking frequency in a certain time period,
    wherein the detecting of the acceleration in the gravitational acceleration direction includes calculating a ratio of acceleration for each coordinate axis, the ratio of acceleration for each coordinate axis corresponding to detected acceleration in each coordinate axis as detected by an acceleration sensor of the portable electronic apparatus being held by the user in a static state with respect to the sum of the detected acceleration in all of the coordinate axes,
    wherein the acceleration in the gravitational acceleration direction of the portable electronic apparatus is calculated based on the calculated ratio of acceleration for each coordinate axis with respect to the gravitational acceleration direction.

* * * * *